US009987481B2

(12) United States Patent
Kaib et al.

(10) Patent No.: US 9,987,481 B2
(45) Date of Patent: *Jun. 5, 2018

(54) ELECTRODE WITH REDUNDANT IMPEDANCE REDUCTION

(71) Applicant: ZOLL MEDICAL CORPORATION, Chelmsford, MA (US)

(72) Inventors: Thomas E. Kaib, North Huntingdon, PA (US); Shane S. Volpe, Saltsburg, PA (US); Emil Oskin, Natrona Heights, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 525 days.

This patent is subject to a terminal disclaimer.

(21) Appl. No.: 14/690,116

(22) Filed: Apr. 17, 2015

(65) Prior Publication Data

US 2015/0217108 A1    Aug. 6, 2015

Related U.S. Application Data

(63) Continuation of application No. 13/849,751, filed on Mar. 25, 2013, now Pat. No. 9,037,271, which is a
(Continued)

(51) Int. Cl.
*A61N 1/37* (2006.01)
*A61N 1/39* (2006.01)
(Continued)

(52) U.S. Cl.
CPC .............. *A61N 1/0496* (2013.01); *A61B 5/04* (2013.01); *A61B 5/6804* (2013.01);
(Continued)

(58) Field of Classification Search
CPC ....... A61B 5/04; A61B 5/6804; A61B 5/6823; A61B 2562/14; A61N 1/0496; A61N 1/046; A61N 1/3925; A61N 1/39–1/395
See application file for complete search history.

(56) References Cited

U.S. PATENT DOCUMENTS 3,467,863 A   9/1969   Karsh
4,058,127 A   11/1977  Buchalter
(Continued)

FOREIGN PATENT DOCUMENTS

DE   2644236 A1   4/1978
EP   00339471 A2  11/1989
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.
(Continued)

*Primary Examiner* — Lee S Cohen
*Assistant Examiner* — Erin M Cardinal
(74) *Attorney, Agent, or Firm* — Lando & Anastasi, LLP

(57) ABSTRACT

An electrode assembly that includes an electrically conductive layer, a first impedance reduction system, and a second impedance reduction system. The electrically conductive layer forms an electrode portion of the electrode assembly and a first surface to be placed adjacent a person's skin. The first impedance reduction system is configured to dispense a first amount of an electrically conductive gel onto the first surface of the electrically conductive layer in response to a first activation signal. The second impedance reduction system is configured to dispense a second amount of the electrically conductive gel onto the first surface of the electrically conductive layer in response to a second activation signal.

21 Claims, 4 Drawing Sheets

Related U.S. Application Data continuation of application No. 13/315,937, filed on Dec. 9, 2011, now Pat. No. 8,406,842, which is a continuation of application No. PCT/US2011/063931, filed on Dec. 8, 2011.

(60) Provisional application No. 61/421,283, filed on Dec. 9, 2010, provisional application No. 61/421,283, filed on Dec. 9, 2010.

(51) Int. Cl.
| | |
|---|---|
| A61N 1/04 | (2006.01) |
| A61B 5/0408 | (2006.01) |
| A61B 5/04 | (2006.01) |
| A61M 35/00 | (2006.01) |
| A61B 5/00 | (2006.01) |
| A61N 1/08 | (2006.01) |

(52) U.S. Cl.
CPC ........... *A61M 35/003* (2013.01); *A61N 1/046* (2013.01); *A61B 5/6823* (2013.01); *A61B 2562/14* (2013.01); *A61N 1/39* (2013.01); *A61N 1/3925* (2013.01); *A61N 2001/083* (2013.01)

(56) References Cited

U.S. PATENT DOCUMENTS

| | | |
|---|---|---|
| 4,094,310 A | 6/1978 | McEachern et al. |
| 4,464,412 A | 8/1984 | Washburn |
| 4,632,122 A | 12/1986 | Johansson et al. |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,080,097 A * | 1/1992 | Eisenberg .............. A61N 1/046 607/2 |
| 5,348,008 A | 9/1994 | Bornn et al. |
| 5,365,932 A | 11/1994 | Greenhut |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,065,154 A | 5/2000 | Hulings et al. |
| 6,097,982 A | 8/2000 | Glegyak et al. |
| 6,097,987 A | 8/2000 | Milani |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,908,437 B2 | 6/2005 | Bardy |
| 6,990,373 B2 | 1/2006 | Jayne et al. |
| 7,149,579 B1 | 12/2006 | Koh et al. |
| 7,206,630 B1 | 4/2007 | Tarler |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,831,303 B2 | 11/2010 | Rueter et al. |
| 7,970,451 B2 | 6/2011 | Hassonjee et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,406,842 B2 * | 3/2013 | Kaib .................. A61B 5/04 600/382 |
| 8,880,196 B2 | 11/2014 | Kaib |
| 9,008,801 B2 | 4/2015 | Kaib et al. |
| 2003/0004547 A1 | 1/2003 | Owen et al. |
| 2003/0095648 A1 | 5/2003 | Kaib et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2005/0049515 A1 | 3/2005 | Misczynski et al. |
| 2005/0131465 A1 | 6/2005 | Freeman et al. |
| 2005/0136077 A1 * | 6/2005 | Yahiaoui ............ A61B 5/04087 424/401 |
| 2006/0036292 A1 | 2/2006 | Smith et al. |
| 2006/0085049 A1 | 4/2006 | Cory et al. |
| 2006/0270952 A1 | 11/2006 | Freeman et al. |
| 2007/0118056 A1 | 5/2007 | Wang et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2008/0000006 A1 | 1/2008 | Ochoa et al. |
| 2008/0004536 A1 | 1/2008 | Baxi et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0249591 A1 | 10/2008 | Gaw et al. |
| 2008/0306560 A1 | 12/2008 | Macho et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0234716 A1 | 9/2010 | Engel |
| 2010/0298899 A1 | 11/2010 | Donnelly et al. |
| 2011/0028822 A1 | 2/2011 | Beck |
| 2011/0288604 A1 | 11/2011 | Kaib et al. |
| 2011/0288605 A1 | 11/2011 | Kaib et al. |
| 2011/0312644 A1 | 12/2011 | Silverbrook et al. |
| 2012/0011382 A1 | 1/2012 | Volpe et al. |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2013/0144357 A1 | 6/2013 | Forward |
| 2014/0213875 A1 | 7/2014 | Freeman et al. |
| 2015/0045870 A1 | 2/2015 | Kaib |

FOREIGN PATENT DOCUMENTS

| | | |
|---|---|---|
| EP | 0295497 B1 | 9/1993 |
| EP | 0335356 B1 | 3/1996 |
| EP | 1455640 B1 | 1/2008 |

(56) References Cited

FOREIGN PATENT DOCUMENTS

| EP | 1720446 B1 | 7/2010 |
|---|---|---|
| JP | 5115450 A | 5/1993 |
| WO | 200002484 A1 | 1/2000 |
| WO | 2004054656 A1 | 7/2004 |
| WO | 2008116822 A2 | 10/2008 |

OTHER PUBLICATIONS

DeBock, et al., "Captopril treatment of chronic heart failure in the very old," J. Gerontol. (1994) 49: M148-M152.

International Search Report issued for PCT/US2011/063931 dated Aug. 23, 2012, pp. 1-3.

O'Keeffe et al., "Reproducability and responsiveness of quality of life assessment and six minute walk test in elderly heart failure patients," Heart (1998) 80: 377-382.

\* cited by examiner

ELECTRODE WITH REDUNDANT IMPEDANCE REDUCTION

CROSS REFERENCE TO RELATED APPLICATIONS

This application claims the benefit under 35 U.S.C. § 120 as a continuation of U.S. application Ser. No. 13/849,751 titled "ELECTRODE WITH REDUNDANT IMPEDANCE REDUCTION" filed Mar. 25, 2013, now U.S. Pat. No. 9,037,271 issued May 19, 2015, which claims the benefit under 35 U.S.C. § 120 as a continuation of U.S. application Ser. No. 13/315,937 titled "ELECTRODE WITH REDUNDANT IMPEDANCE REDUCTION" filed Dec. 9, 2011, now U.S. Pat. No. 8,406,842 issued Mar. 26, 2013, which claims priority under 35 U.S.C. § 120 as a continuation of International Patent Application Serial No. PCT/US2011/063931, titled "ELECTRODE WITH REDUNDANT IMPEDANCE REDUCTION" filed Dec. 8, 2011, which claims priority under 35 U.S.C. § 119(e) to U.S. Provisional Application Ser. No. 61/421,283 titled "ELECTRODE WITH REDUNDANT IMPEDANCE REDUCTION" filed Dec. 9, 2010. U.S. application Ser. No. 13/315,937 titled "ELECTRODE WITH REDUNDANT IMPEDANCE REDUCTION" filed Dec. 9, 2011, also claims priority under 35 U.S.C. § 119(e) to U.S. Provisional Application Ser. No. 61/421,283 titled "ELECTRODE WITH REDUNDANT IMPEDANCE REDUCTION" filed Dec. 9, 2010.

BACKGROUND OF THE INVENTION

1. Field of the Invention

The present invention is directed to medical electrodes, and more particularly, to a medical electrode with redundant impedance reduction systems that may be used with a wearable medical device, such as a defibrillator.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk patients may use a wearable defibrillator, such as the LifeVest® wearable cardioverter defibrillator available from Zoll Medical Corporation of Chelmsford, Mass. To remain protected, the patient wears the device nearly continuously while going about their normal daily activities, while awake, and while asleep.

SUMMARY OF THE INVENTION

In accordance with one aspect of the present invention, an electrode assembly is provided. The electrode assembly comprises an electrically conductive layer that forms an electrode portion of the electrode assembly, a first impedance reduction system, and a second impedance reduction system. The electrically conductive layer has a first surface to be placed adjacent a person's skin. The first impedance reduction system is configured to dispense a first amount of a first electrically conductive gel onto the first surface of the electrically conductive layer in response to a first activation signal, and the second impedance reduction system is configured to dispense a second amount of a second electrically conductive gel onto the first surface of the electrically conductive layer in response to a second activation signal.

In accordance with one embodiment, the first activation signal and the second activation signal are based upon the same signal. In accordance with another embodiment, the first activation signal is distinct from the second activation signal.

In accordance with an aspect of the present invention, the second impedance reduction system is configured to dispense the second amount of the second electrically conductive gel onto the first surface of the electrically conductive layer in response to the second activation signal and independent of whether the first impedance reduction system dispenses the first amount of the first electrically conductive gel on the first surface of the electrically conductive layer in response to the first activation signal.

In accordance with one embodiment, the first impedance reduction system is similar in construction to the second impedance reduction system.

In accordance with one embodiment, the electrically conductive layer has a plurality of apertures formed there through, the plurality of apertures including a first plurality of apertures and a second plurality of apertures. In accordance with this embodiment, the first impedance reduction system is configured to dispense the first amount of the first electrically conductive gel through the first plurality of apertures and onto the first surface of the electrically conductive layer in response to the first activation signal, and the second impedance reduction system is configured to dispense the second amount of the second electrically conductive gel through the second plurality of apertures and onto the first surface of the electrically conductive layer in response to the second activation signal. In one embodiment, the first electrically conducting gel and the second electrically conducting gel are the same type of electrically conducting gel.

In accordance with another aspect of the present invention, an electrode assembly is provided. The electrode assembly comprises an electrically conductive layer, a first plurality of gel reservoirs, a second plurality of gel reservoirs, a first fluid channel, a second fluid channel, a first fluid pressure source, and a second fluid pressure source. The electrically conductive layer has a plurality of apertures formed therein, the plurality of apertures including a first plurality of apertures and a second plurality of apertures. The first plurality of gel reservoirs each contain a first electrically conductive gel, each respective gel reservoir of the first plurality of gel reservoirs having an outlet to fluidly communicate with a respective aperture of the first plurality of apertures. The second plurality of gel reservoirs each contain a second electrically conductive gel, each respective gel reservoir of the second plurality of gel reservoirs having an outlet to fluidly communicate with a respective aperture of the second plurality of apertures. The first fluid channel is in fluid communication with each of the first plurality of gel reservoirs, and the second fluid channel is in fluid communication with each of the second plurality of gel reservoirs. The first fluid pressure source is in fluid communication with the first fluid channel and configured to receive a first activation signal and force a first fluid under pressure into the first fluid channel in response to the first activation signal, and the second fluid pressure source is in fluid communication with the second fluid channel and configured to receive a second activation signal and force a second fluid under pressure into the second fluid channel in response to the second activation signal.

In accordance with one embodiment, the outlet of each of the first plurality of gel reservoirs and the outlet of each of the second plurality of gel reservoirs is sealed by a membrane that is constructed to rupture in response to the pressure of the first fluid and the second fluid, respectively.

In accordance with one embodiment, the first activation signal and the second activation signal are based upon the same signal. In another embodiment, the first activation signal is distinct from the second activation signal.

In accordance with another aspect of the present invention, an electrode assembly is provided that comprises at least one ECG sensing electrode, a therapy electrode, a first impedance reduction system and a second impedance reduction system. The at least one ECG sensing electrode is configured to monitor an ECG signal of a patient and the therapy electrode is configured to deliver a defibrillating shock to the patient. The first impedance reduction system is configured to reduce an impedance between the therapy electrode and the patient in response to a first activation signal, and the second impedance reduction system is configured to reduce the impedance between the therapy electrode and the patient in response to a second activation signal. In accordance with one embodiment, the at least one ECG sensing electrode is electrically insulated from the therapy electrode.

In accordance with one embodiment, the at least one ECG sensing electrode includes a plurality of ECG sensing electrodes. In accordance with a further aspect of this embodiment, each of the plurality of ECG sensing electrodes is electrically insulated from the therapy electrode.

In accordance with one embodiment, the electrode assembly further comprises at least one additional sensor configured to monitor a physiological parameter of the patient that is other than the ECG signal of the patient.

In accordance with one embodiment, the first activation signal and the second activation signal are based upon the same signal, and the first impedance reduction system is similar in construction to the second impedance reduction system.

In accordance with one embodiment, the therapy electrode includes an electrically conductive layer having a first surface to be placed adjacent a person's skin and a plurality of apertures formed through the electrically conductive layer. The plurality of apertures includes a first plurality of apertures and a second plurality of apertures. The first impedance reduction system is configured to dispense a first amount of a first electrically conductive gel through the first plurality of apertures and onto the first surface of the electrically conductive layer in response to the first activation signal, and the second impedance reduction system is configured to dispense a second amount of a second electrically conductive gel through the second plurality of apertures and onto the first surface of the electrically conductive layer in response to the second activation signal.

In accordance with another aspect of the present invention, a method of reducing impedance between an electrode and a patient's skin is provided. The method comprises acts of sending a first activation signal to a first impedance reduction system configured to dispense a first amount of a first electrically conducting gel onto a surface of the electrode that is configured to be disposed adjacent the patient's skin, and sending a second activation signal to a second impedance reduction system configured to dispense a second amount of a second electrically conducting gel onto the surface of the electrode that is configured to be disposed adjacent the patient's skin, the second impedance reduction system being distinct from the first impedance reduction system.

In accordance with one embodiment, the method further comprises an act of determining whether the first impedance reduction system dispensed the first amount of the first electrically conducting gel onto the surface of the electrode, wherein the act of sending the second activation signal to the second impedance reduction system is performed in response to a determination that the first impedance reduction system did not dispense the first amount of the first electrically conducting gel onto the surface of the electrode. In accordance with one embodiment, the act of sending the second activation signal is performed subsequent to the act of sending the first activation signal. In an alternative embodiment, the act of sending the second activation signal is performed substantially simultaneously with the act sending the first activation signal.

Still other aspects, embodiment, and advantages of these exemplary aspects and embodiments are discussed in detail below. Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with aspects of the present invention disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearance of such terms herein is not necessarily all referring to the same embodiment.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2b is a functional block diagram of an impedance reduction system that may be included in the electrode portion of FIG. 2a;

DETAILED DESCRIPTION

Figure 1:
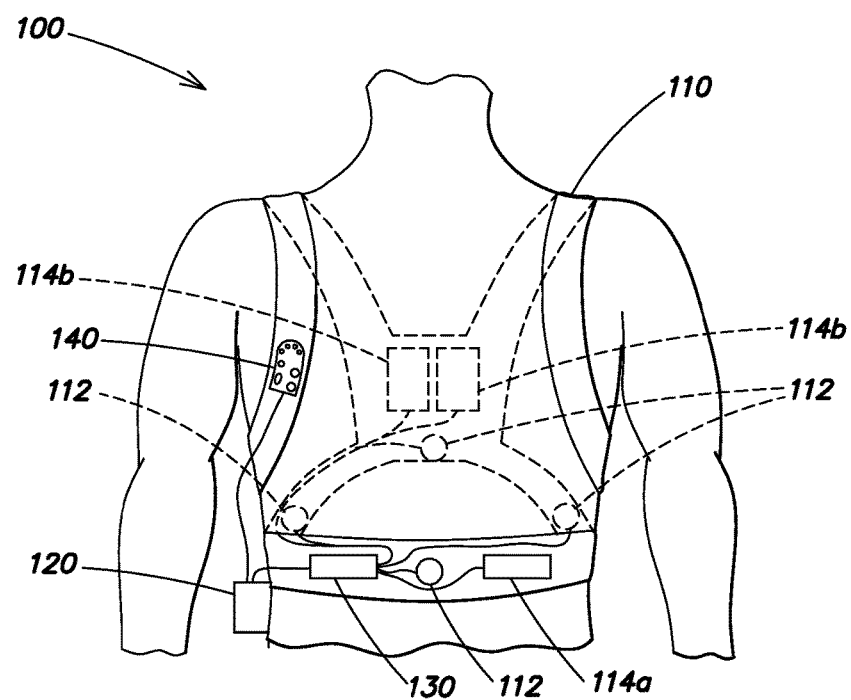
FIG. 1 illustrates a wearable medical device, such as a wearable defibrillator.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

FIG. 1 illustrates a wearable medical device, such as a LifeVest® wearable cardioverter defibrillator available from Zoll Medical Corporation of Chelmsford, Mass. As shown, the wearable medical device 100 includes a harness 110 having a pair of shoulder straps and a belt that is worn about the torso of a patient. The harness 110 is typically made from a material, such as cotton, that is breathable, and unlikely to cause skin irritation, even when worn for prolonged periods of time. The wearable medical device 100 includes a plurality of ECG sensing electrodes 112 that are attached to the harness 110 at various positions about the patient's body and electrically coupled to a control unit 120 via a connection pod 130. The plurality of ECG sensing electrodes 112, which may be dry-sensing capacitance electrodes, are used by the control unit 120 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the control unit 120 via the connection pod 130 and which are capable of delivering one or more therapeutic defibrillating shocks to the body of the patient, if it is determined that such treatment is warranted. As shown, the plurality of therapy electrodes 114 includes a first therapy electrode 114a that is disposed on the front of the patient's torso and a second therapy electrode 114b that is disposed on the back of the patient's torso. The second therapy electrode 114b includes a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod 130 electrically couples the plurality of ECG sensing electrodes 112 and the plurality of therapy electrodes 114 to the control unit 120, and may include electronic circuitry. For example, in one implementation the connection pod 130 includes signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may also include other electronic circuitry, such as a motion sensor or accelerometer by which patient activity may be monitored.

As shown in FIG. 1, the wearable medical device 100 also includes a user interface pod 140 that is electrically coupled to the control unit 120. The user interface pod 140 can be attached to the patient's clothing or to the harness 110, for example, via a clip (not shown) that is attached to a portion of the interface pod 140. Alternatively, the user interface pod 140 may simply be held in a person's hand. In some embodiments, the user interface pod 140 may communicate wirelessly with the control unit 120, for example, using a Bluetooth®, Wireless USB, ZigBee, Wireless Ethernet, GSM, or other type of communication interface. The user interface pod 140 typically includes a number of buttons by which the patient, or a bystander can communicate with the control unit 120, and a speaker by which the control unit 120 may communicate with the patient or the bystander. For example, where the control unit 120 determines that the patient is experiencing cardiac arrhythmia, the control unit 120 may issue an audible alarm via a loudspeaker (not shown) on the control unit 120 and/or the user interface pod 140 alerting the patient and any bystanders to the patient's medical condition. The control unit 120 may also instruct the patient to press and hold one or more buttons on the control unit 120 or on the user interface pod 140 to indicate that the patient is conscious, thereby instructing the control unit 120 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient. In some embodiments, the functionality of the user interface pod 140 may be integrated into the control unit 120.

The control unit 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that comprises a general purpose processor, such as an Intel® PXA270 processor and a special purpose processor, such as a Freescale™ DSP56311 Digital Signal Processor. Such a power conserving processor arrangement is described in co-pending application Ser. No. 12/833,096, entitled SYSTEM AND METHOD FOR CONSERVING POWER IN A MEDICAL DEVICE, filed Jul. 9, 2010 (hereinafter the "'096 application") which is incorporated by reference herein in its entirety. The at least one processor of the control unit 120 is configured to monitor the patient's medical condition, to perform medical data logging and storage, and to provide medical treatment to the patient in response to a detected medical condition, such as cardiac arrhythmia. Although not shown, the wearable medical device 100 may include additional sensors, other than the ECG sensing electrodes 112, capable of monitoring the physiological condition or activity of the patient. For example, sensors capable of measuring blood pressure, heart rate, thoracic impedance, pulse oxygen level, respiration rate, heart sounds, and the activity level of the patient may also be provided.

As discussed above, to provide protection against cardiac arrest, patients that use a wearable medical device, such as a wearable defibrillator, generally wear the device nearly continuously while they are awake and while they are asleep. Because the wearable medical device is worn nearly continuously, dry electrodes are typically used for both the plurality of ECG sensing electrodes 112 and the plurality of therapy electrodes 114 for comfort and to prevent irritation of the patient's skin. Where it is determined that one or more defibrillating shocks are to be delivered to the body of the patient and the patient is non-responsive, the control unit 120 sends a signal to the plurality of therapy electrodes 114 causing them to release an impedance reducing gel prior to delivery of one or more defibrillating shocks. The impedance reducing gel reduces the impedance between the conductive surface of the therapy electrodes and the patient's skin, thereby improving the efficiency of the energy delivered to the patient and reducing the chance of damage (e.g., in the form of burning, reddening, or other types of irritation) to the patient's skin.

Figure 2A:
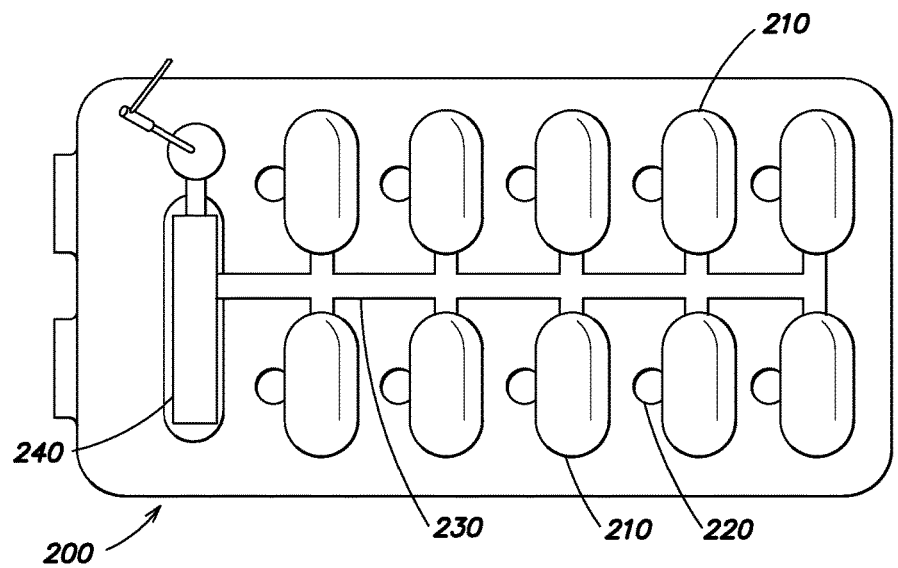
FIG. 2a is a plan view of an electrode portion of a therapy electrode assembly that may be used with the wearable medical device illustrated in FIG. 1.
Figure 2B:
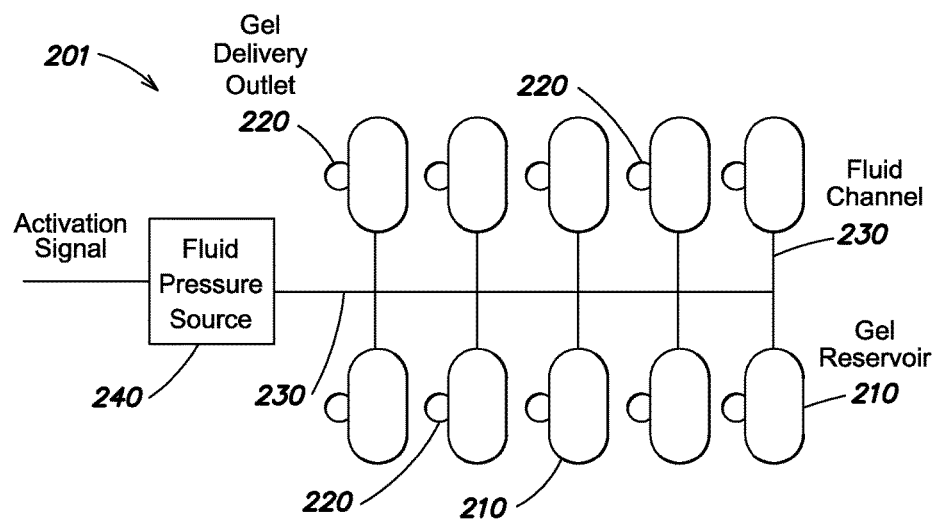

FIG. 2a is a plan view of an electrode portion of a therapy electrode assembly that includes an impedance reduction system and which may be used with a wearable medical device, such as the wearable defibrillator described above with respect to FIG. 1. FIG. 2b is a functional block diagram of the impedance reduction system that is included in the electrode portion of the therapy electrode assembly shown in FIG. 2a. The impedance reduction system, when activated, dispenses an impedance reducing (i.e., electrically conductive) gel onto the exposed surface of the electrode portion of the therapy electrode assembly that, in use, is placed most proximate to the patient's body. The electrode portion 200 is a multiple layer laminated structure that includes an electrically conductive layer (not visible in FIG. 2a, but disposed adjacent the bottom surface of the electrode portion 200 shown in FIG. 2a) that forms the electrode and an impedance reduction system 201. In use, the electrically conductive layer is disposed adjacent the patient's skin, although the conductive layer need not make direct contact with the patient, as portions of the harness 110 (FIG. 1) and/or portions of the patient's clothing may be present between the electrically conductive layer and the patient's skin. As shown in FIG. 2a, the impedance reduction system 201 is disposed on a side of the electrode portion 200 (i.e., the top-side shown in FIG. 2a) that is opposite the side on which the conductive layer is formed.

The impedance reduction system 201 includes a plurality of conductive gel reservoirs 210, each of which has a respective gel delivery outlet 220, that are fluidly coupled to a fluid channel 230, and a fluid pressure source 240. The fluid pressure source 240 is fluidly coupled to the fluid channel 230, and when activated by an activation signal, forces a fluid, such as Nitrogen gas, into the channel 230. The hydraulic pressure of the fluid from the activated fluid pressure source 240 in the fluid channel 230 forces the conductive gel stored in each of the plurality of gel reservoirs out of the plurality of gel delivery outlets 220 through apertures formed in the electrically conductive layer and onto the exposed surface of the electrically conductive layer that, in use, is placed most proximate to the patient's body. The apertures in the electrically conductive layer are generally aligned with the plurality of gel delivery outlets 220 so that when activated, the electrically conductive gel is dispensed onto the exposed surface of the electrode portion that is disposed most proximate to the patient's body. Further details regarding the construction of the electrode portion 200 are described in U.S. Pat. No. 5,078,134 (hereinafter "the '134 patent") which is incorporated herein by reference.

Applicants have appreciated that there may be instances where it would be desirable to have redundancy in the impedance reduction system described above. An electrode that incorporates redundant impedance reduction systems is now described with respect to FIGS. 3-5 below.

Figure 3:
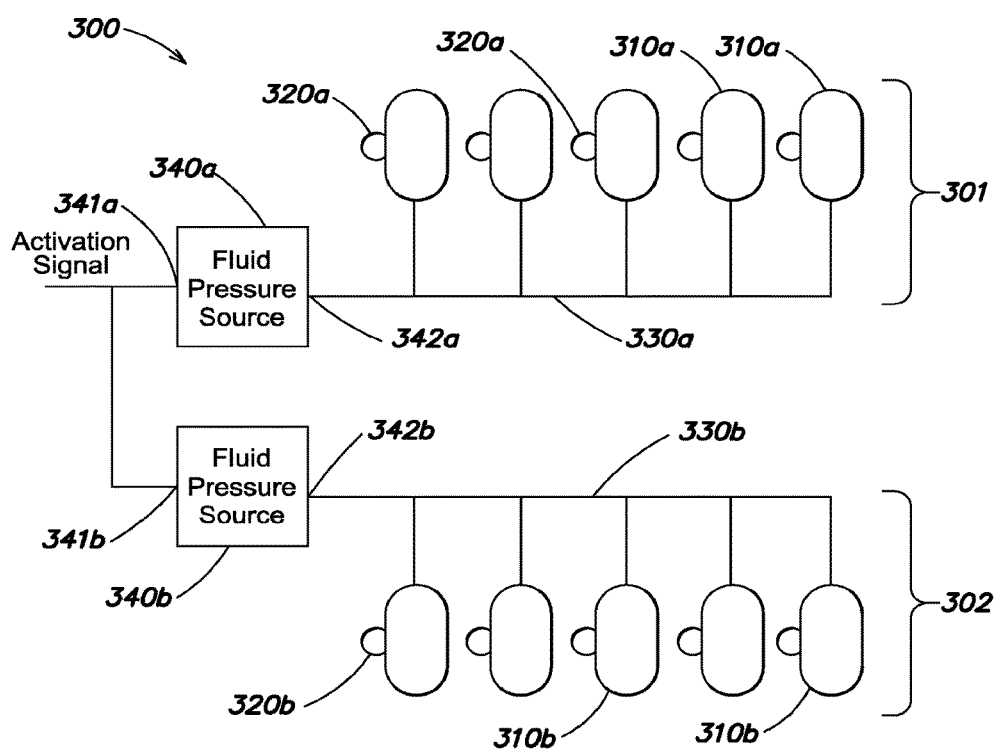
FIG. 3 is a functional block diagram of a redundant impedance reduction system in accordance with an aspect of the present invention.

FIG. 3 is a functional block diagram of a redundant impedance reduction system that may be incorporated in an electrode assembly in accordance with an aspect of the present invention. As shown, the redundant impedance reduction system 300 includes at least two independent impedance reduction systems 301, 302 similar in construction and operation to that described previously with respect to FIGS. 2a and 2b. Although only two impedance reduction systems 301, 302 are shown in FIG. 3, it should be appreciated that additional impedance reduction systems may be provided.

As shown, a first impedance reduction system 301 of the at least two impedance reduction systems 301, 302 includes a first plurality of gel reservoirs 310a, each containing an electrically conductive gel, with each respective gel reservoir including a gel delivery outlet 320a. Each of the first plurality of gel reservoirs 310a is fluidly coupled to a first fluid channel 330a that is, in turn, fluidly coupled to a first fluid pressure source 340a. The first fluid pressure source 340a has an input 341a to receive a first electrical activation signal and a fluid outlet 342a that is fluidly coupled to the first fluid channel 330a. A rupturable membrane and/or a filter (not shown) may be positioned between the fluid outlet 342a and the first fluid channel 330a as described in the '134 patent. As described in the '134 patent, the first fluid pressure source 340a may include a gas generating cartridge that ignites a chemical pellet (such as a Lead Styphnate igniter and a gas generating mixture of Ammonium Dichromate and Nitroguanidine) that rapidly decomposes and generates quantities of a gas, such as Nitrogen. It should be appreciated that other types of fluid pressure sources may be used, as the present invention is not limited to any particular type of fluid pressure source.

In response to the first activation signal received at the input 341a of the first fluid pressure source 340a, a fluid, such as Nitrogen gas, is forced into the first fluid channel 330a and then into each of the first plurality of gel reservoirs 310a. The hydraulic pressure of the fluid flowing into each of the first plurality of gel reservoirs 310a forces the electrically conductive gel contained in each gel reservoir toward its respective gel delivery outlet 320a, thereby fracturing a membrane separating the gel delivery outlet from a respective aperture formed in the electrically conductive layer of the electrode portion.

The second impedance reduction system 302 of the at least two impedance reduction systems 301, 302 is similar to the first impedance reduction system 301 and includes a second plurality of gel reservoirs 310b, each containing an electrically conductive gel, with each respective gel reservoir including a gel delivery outlet 320b. The electrically conductive gel contained in the second plurality of gel reservoirs 310b may, but need not, be the same type of gel as that contained in the first plurality of gel reservoirs 310a. For example, the electrically conductive gel contained in the second plurality of gel reservoirs 310b may have a different color, or have a longer drying time than the gel contained in the first plurality of gel reservoirs 310a. Each of the plurality of gel reservoirs 310b is fluidly coupled to a second fluid channel 330b that is, in turn, fluidly coupled to a second fluid pressure source 340b. The second fluid pressure source 340b has an input 341b to receive a second electrical activation signal and a fluid outlet 342b that is fluidly coupled to the second fluid channel 330b. The second fluid pressure source 340b may similar in construction to the first fluid source 340a described above.

As shown in FIG. 3, the input 341a of the first fluid pressure source 340a may be electrically connected to the input 341b of the second fluid pressure source, such that a single activation signal activates each of the at least two impedance reduction systems 301, 302 substantially simultaneously. Should one of the redundant impedance reduction systems 301, 302 fail to operate (either partially or completely), the other can still operate to dispense conductive gel onto the exposed surface of the electrode. The activation signal provided to the input 341a of the first fluid pressure source 340a may be provided by the control unit 120 (FIG. 1) to the first fluid pressure source 340a using an electrical conductor that is physically distinct from that which provides the activation signal to the input 341b of the second fluid pressure source 340b to permit further redundancy, for example, should one of the electrical conductors be damaged. Alternatively, a single electrical conductor may be provided between the control unit 120 and the electrode assembly, with the single electrical conductor being connected to both the input 341a of the first fluid pressure source 340a and the input 341b of the second fluid pressure source 340b.

It should be appreciated that each of the first and second pressure sources 340a, 340b may alternatively receive separate activation signals, as the present invention is not limited to receiving a single activation signal. The separate activation signals may be sent, for example by the control unit 120, to each of the first fluid pressure source 340a and the second fluid pressure source 340b at substantially the same time, or at different times. For example, a first activation signal may be provided to the input 341a of the first fluid pressure source 340a at a first time, and a second activation signal may be provided to the input 341b of the second fluid pressure source 340b at a second time that is subsequent to the first time. In accordance with one embodiment, the control unit 120 (FIG. 1) may send the first activation signal to the first fluid pressure source 340a at a first time, and send the second activation signal to the second fluid pressure source 340b at a second and subsequent time where it is determined that the first impedance reduction system 301 failed to operate. Alternatively, the second activation signal may be sent to the second fluid pressure source 340b at a second and subsequent time even where activation of the first fluid pressure source 340a is successful. Such a subsequent activation of the second fluid pressure source 340b would permit a second deployment of conductive gel onto the exposed surface of the electrode and permit the electrode to maintain a high conductivity with the patient for a longer period of time than if both impedance reduction systems 301, 302 were activated at substantially the same time.

Figure 4:
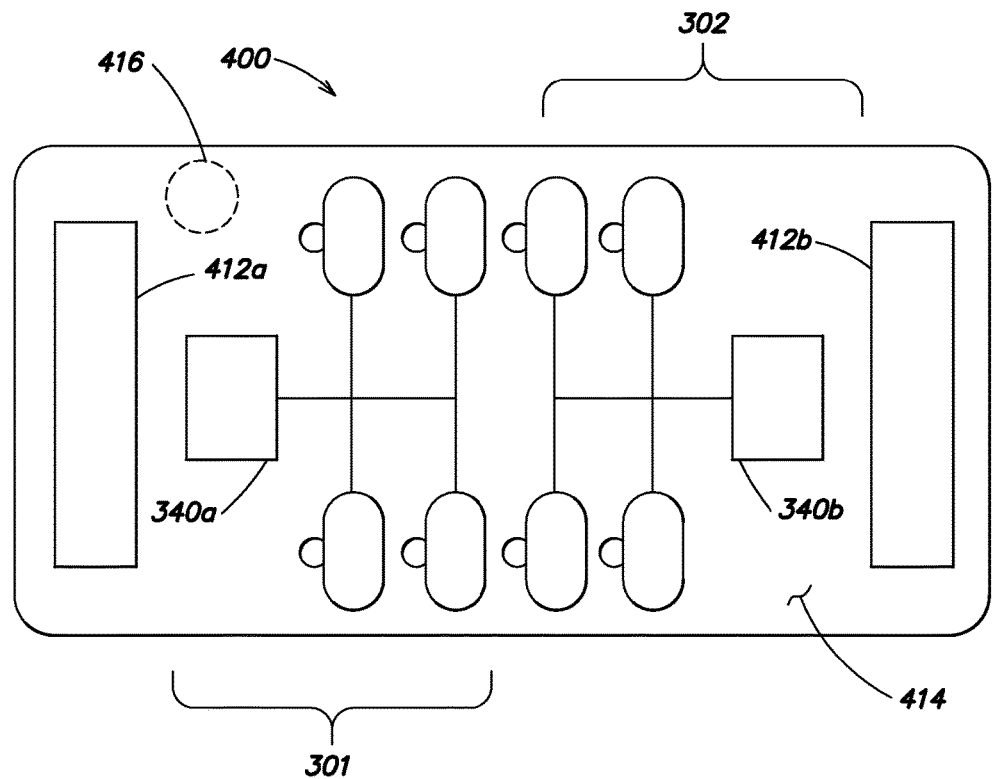
FIG. 4 is a schematic diagram of an electrode assembly that includes ECG sensing electrodes, a therapy electrode, and redundant impedance reduction systems in accordance with another aspect of the present invention.

FIG. 4 illustrates an electrode assembly that combines one or more ECG sensing electrodes, a therapy electrode, and redundant impedance reduction systems in a single integrated electrode assembly in accordance with a further aspect of the present invention. As shown, the electrode assembly 400 includes a pair of ECG sensing electrodes 412a, 412b for monitoring the cardiac function of a patient. The electrode assembly 400 further includes a therapy electrode 414, and at least two impedance reduction systems 301, 302, similar to those described previously with respect to FIG. 3. The pair of ECG sensing electrodes 412a, 412b may be electrically separated from the therapy electrode 414, for example, by an insulator. It should be appreciated that in other embodiments, the electrode assembly 400 may include only a single ECG sensing electrode, while in other embodiments, more than two ECG sensing electrodes may be provided. In such alternative embodiments, the number and placement of ECG sensing electrodes and may vary from that shown in FIG. 4. In yet a further embodiment, the integrated electrode assembly can include additional sensors 416, other than the one or more ECG sensing electrodes and the therapy electrode, that are capable of monitoring other physiological parameters of a patient, such as blood pressure, heart rate, thoracic impedance, pulse oxygen level, respiration rate, heart sounds, etc.

Figure 5:
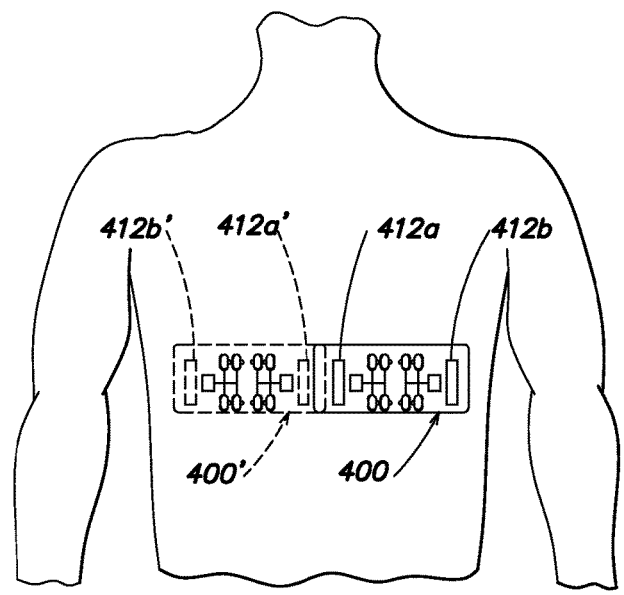
FIG. 5 illustrates the manner in which the electrode assembly of FIG. 4 may be worn on the body of a patient.

The electrode assembly 400 may be worn on the patient's body such that one of the pair of ECG sensing electrodes 412a, 412b is disposed approximately in the center of the patient's torso, and the other of the pair of ECG sensing electrodes 412a, 412b is disposed on the side of the patient's torso. For example, as shown in FIG. 5, the electrode assembly 400 may be worn on the front of the patient's torso, so that the ECG sensing electrode 412a is disposed approximately in the center of the patient's chest, and the other ECG sensing electrode 412b is disposed on the patient's side. A second electrode assembly 400' may be worn on the back of the patient's torso to provide a second pair of ECG sensing electrodes 412a', 412b', so that one of the ECG sensing electrodes (e.g., ECG sensing electrode 412a') of the second pair of ECG sensing electrodes 400' is disposed approximately in the center of the patient's back, and the other ECG sensing electrode (e.g., ECG sensing electrode 412b') of the second pair of ECG sensing electrodes 400' is disposed on the patient's side opposite the other ECG sensing electrode (e.g., ECG sensing electrode 412b) of the first pair of ECG sensing electrodes 412a, 412b, as shown in FIG. 5. Such an arrangement provides a front-to-back pairing of ECG sensing electrodes (e.g., 412a, 412a') and a side-to-side pairing of ECG sensing electrodes (e.g., 412b, 412b'). It should be appreciated that other placements for the first electrode assembly 400 and the second electrode assembly 400' may alternatively be used. For example, the first electrode assembly 400 may be placed on one side of the patient's torso, and the second electrode assembly 400' placed on the other side of the patient's torso to provide side-to-side pairings of ECG sensing electrodes.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A medical device comprising:
   a first impedance reduction system configured to dispense a first amount of a first electrically conductive gel proximate a person's skin;
   a therapy electrode including an electrically conductive layer having a surface configured to be placed adjacent the person's skin, wherein the first impedance reduction system is configured to dispense the first amount of the first electrically conductive gel onto the surface of the electrically conductive layer in response to a first activation signal; and
   a second impedance reduction system configured to dispense a second amount of a second electrically conductive gel proximate the person's skin responsive to a determination that the first impedance reduction system did not dispense the first amount of the first electrically conducting gel, the second impedance reduction system being configured to dispense the second amount of the second electrically conductive gel onto the surface of the electrically conductive layer in response to a second activation signal that is distinct from the first activation signal.

2. The medical device of claim 1, further comprising a control unit configured to send the second activation signal responsive to a determination that the first impedance reduction system failed to operate.

3. The medical device of claim 1, wherein the second impedance reduction system is further configured to dispense the second amount of the second electrically conductive gel in response to the second activation signal and independent of whether the first impedance reduction system dispenses the first amount of the first electrically conductive gel in response to the first activation signal.

4. The medical device of claim 1, wherein the electrically conductive layer has a plurality of apertures formed therethrough, the plurality of apertures including a first plurality of apertures and a second plurality of apertures, wherein the first impedance reduction system is configured to dispense the first amount of the first electrically conductive gel through the first plurality of apertures, and wherein the second impedance reduction system is configured to dispense the second amount of the second electrically conductive gel through the second plurality of apertures.

5. The medical device of claim 1, wherein the second electrically conductive gel has at least one property different from the first electrically conductive gel.

6. The medical device of claim 1, wherein the second electrically conductive gel has a longer drying time than the first electrically conductive gel.

7. The medical device of claim 1, wherein the medical device is a wearable medical device and the first impedance reduction system and the second impedance reduction system are disposed in the wearable medical device.

8. A medical device comprising:
at least one therapy electrode disposed in a wearable medical device, the at least one therapy electrode having an electrically conductive surface configured to provide electrical therapy to a person, the at least one therapy electrode having at least one first aperture and at least one second aperture formed in the electrically conductive surface of the at least one therapy electrode;
a first impedance reduction system configured to dispense a first amount of a first electrically conductive gel out the at least one first aperture and onto the electrically conductive surface of the at least one therapy electrode in response to a first activation signal;
a second impedance reduction system configured to dispense a second amount of a second electrically conductive gel out the at least one second aperture and onto the electrically conductive surface of the at least one therapy electrode in response to a second activation signal that is distinct from the first activation signal; and
a control unit configured to send the second activation signal to the second impedance reduction system responsive to a determination that the first impedance reduction system failed to dispense the first amount of the first electrically conductive gel.

9. The medical device of claim 8, wherein the first impedance reduction system and the second impedance reduction system are disposed on the at least one therapy electrode.

10. The medical device of claim 8, wherein the at least one first aperture includes a plurality of first apertures and the at least one second aperture includes a plurality of second apertures.

11. The medical device of claim 10, wherein the at least one therapy electrode includes a first plurality of gel reservoirs containing the first electrically conductive gel and a second plurality of gel reservoirs containing the second electrically conductive gel, each respective gel reservoir of the first plurality of gel reservoirs having an outlet in fluid communication with a respective aperture of the plurality of first apertures, and each respective gel reservoir of the second plurality of gel reservoirs having an outlet in fluid communication with a respective aperture of the plurality of second apertures.

12. The medical device of claim 11, wherein the first impedance reduction system includes a first fluid pressure source in fluid communication with the first plurality of gel reservoirs and configured to receive the first activation signal and force a first fluid under pressure into the first plurality of gel reservoirs in response to receiving the first activation signal, and wherein the second impedance reduction system includes a second fluid pressure source in fluid communication with the second plurality of gel reservoirs and configured to receive the second activation signal and force a second fluid under pressure into the second plurality of gel reservoirs in response to receiving the second activation signal.

13. The medical device of claim 8, wherein the first impedance reduction system includes a at least one first gel reservoir sealed by a membrane, and the second impedance reduction system includes at least one second gel reservoir sealed by a membrane.

14. The medical device of claim 13, wherein the first impedance reduction system includes a first fluid pressure source configured to pressurize a first fluid in response to the first activation signal and the second impedance reduction system includes a second fluid pressure source configured to pressurize a second fluid in response to the second activation signal, the membrane of the at least one first gel reservoir and the membrane of the at least one second gel reservoir constructed to rupture in response to the pressure of the first fluid and the second fluid, respectively.

15. A method of reducing impedance between a medical device and a person's skin, comprising acts of:
sending a first activation signal to a first impedance reduction system configured to dispense, in response to receipt of the first activation signal, a first amount of a first electrically conductive gel onto a surface of an electrically conductive layer of a therapy electrode configured to be placed adjacent the person's skin; and
sending, responsive to a determination that the first impedance reduction system did not dispense the first amount of the first electrically conductive gel, a second activation signal that is distinct from the first activation signal to a second impedance reduction system configured to dispense, in response to receipt of the second activation signal, a second amount of a second electrically conductive gel onto the surface of the electrically conductive layer.

16. The method of claim 15, wherein the act of sending the second activation signal is performed independent of whether the first impedance reduction system dispensed the first amount of the first electrically conductive gel onto the surface of the electrode.

17. The method of claim 16, wherein the act of sending the first activation signal is performed at a first time, and wherein the act of sending the second activation signal is performed at a second time that is substantially after the first time to maintain an impedance between the electrode and the patient's skin in a reduced state for an extended duration.

18. The method of claim 15, wherein the electrically conductive layer has a first plurality of apertures, and the method further comprises dispensing the first amount of the first electrically conductive gel through the first plurality of apertures onto the electrically conductive layer in response to the first activation signal.

19. The method of claim 18, wherein the electrically conductive layer includes a second plurality of apertures, and the method further comprises dispensing the second amount of the second electrically conductive gel through the second plurality of apertures onto the electrically conductive layer in response to the second activation signal.

20. The method of claim 15, further comprising activating a first fluid pressure source in fluid communication with at least one first gel reservoir to force the first amount of the first electrically conductive gel onto the electrically conductive layer of the therapy electrode in response to receiving the first activation signal.

21. The method of claim 20, further comprising activating a second fluid pressure source in fluid communication with at least one second gel reservoir to force the second amount of the second electrically conductive gel onto the electrically conductive layer of the therapy electrode in response to receiving the second activation signal.

* * * * *